United States Patent
Skerl et al.

(10) Patent No.: US 8,792,970 B2
(45) Date of Patent: Jul. 29, 2014

(54) SYSTEM AND METHOD FOR ANALYZING AN IMPEDANCE COURSE

(75) Inventors: Olaf Skerl, Bad Doberan (DE); Michael Lippert, Ansbach (DE); Gerald Czygan, Buckenhof (DE); Stefan Paule, Drosendorf (DE)

(73) Assignee: BIOTRONIK CRM Patent AG, Baar (CH)

( * ) Notice: Subject to any disclaimer, the term of this patent is extended or adjusted under 35 U.S.C. 154(b) by 1138 days.

(21) Appl. No.: 12/389,719

(22) Filed: Feb. 20, 2009

(65) Prior Publication Data

US 2009/0216145 A1   Aug. 27, 2009

(30) Foreign Application Priority Data

Feb. 22, 2008  (DE) .......................... 10 2008 010 651

(51) Int. Cl.
*A61B 5/04* (2006.01)
*A61B 5/08* (2006.01)
*A61N 1/365* (2006.01)
*A61B 5/053* (2006.01)
*A61N 1/372* (2006.01)

(52) U.S. Cl.
CPC .......... *A61B 5/0809* (2013.01); *A61N 1/36521* (2013.01); *A61B 5/0535* (2013.01); *A61N 1/37258* (2013.01)
USPC ....................................... 600/509

(58) Field of Classification Search
CPC . A61N 1/36521; A61N 1/3702; A61B 5/053; A61B 5/4878; A61B 5/4869; A61B 5/0535; A61B 5/0537; A61B 5/08; A61B 5/0816
USPC ..................... 600/509, 547, 513, 533; 607/20
See application file for complete search history.

(56) References Cited

U.S. PATENT DOCUMENTS

| | | | |
|---|---|---|---|
| 5,876,353 A | 3/1999 | Riff | |
| 5,957,861 A | 9/1999 | Combs | |
| 6,076,015 A | 6/2000 | Hartley | |
| 6,449,509 B1 | 9/2002 | Park | |
| 6,454,719 B1 | 9/2002 | Greenhut | |
| 6,512,949 B1 | 1/2003 | Combs | |
| 7,603,170 B2 * | 10/2009 | Hatlestad et al. | ............. 600/547 |
| 2006/0029360 A1 | 2/2006 | Shiohara | |
| 2006/0041280 A1 | 2/2006 | Stahmann | |
| 2006/0241513 A1 * | 10/2006 | Hatlestad et al. | ............. 600/547 |
| 2006/0258952 A1 | 11/2006 | Stahmann | |
| 2006/0264776 A1 | 11/2006 | Stahmann | |

FOREIGN PATENT DOCUMENTS

| | | |
|---|---|---|
| DE | 3732640 | 5/1989 |
| DE | 102005042923 | 3/2007 |
| EP | 1 665 983 | 6/2006 |

OTHER PUBLICATIONS

German Search Report, dated Jan. 12, 2009, 2 pages.
Yu et al. "Intrathoracic impedance monitoring in patients with heart failure: correlation with fluid status and feasibility of early warning preceding hospitalization." Circulation 2005; 112(6):841-8.
Zipes, D.P. et al. [ed.]: Braunwald's Heart Disease; Elsevier, 2005, 9 pages.
Zima, F, et al. "Determination of left ventricular volume changes by intracardiac conductance using a biventricular electrode configuration." Europace 8.7 (2006): 537-44.
Stahl, C., et al. "Intracardiac Impedance Monitors Hemodynamic Deterioration in a Chronic Heart Failure Pig Model." J. Cardiovasc. Electrophysiol. 18 (2007): 985-90; EP 1 510 173.

* cited by examiner

*Primary Examiner* — Christopher D Koharski
*Assistant Examiner* — Roland Dinga
(74) *Attorney, Agent, or Firm* — ARC IP Law, PC; Joseph J. Mayo (57) ABSTRACT

A system which generates a warning signal in the event of looming pulmonary edema and/or looming decompensation. The system has an impedance detection unit for determining impedance values, which represent a transthoracic impedance course, and an impedance analysis unit (78), which is connected to the impedance detection unit. The impedance analysis unit (78) is implemented to determine the degree of modulation for a particular impedance course detected by the impedance detection unit.

12 Claims, 8 Drawing Sheets

SYSTEM AND METHOD FOR ANALYZING AN IMPEDANCE COURSE

This application takes priority from German Patent Application DE 10 2008 010 651.8, filed 22 Feb. 2008, the specification of which is hereby incorporated herein by reference.

BACKGROUND OF THE INVENTION

1. Field of the Invention

The invention relates to an implant having an impedance detection unit for determining a transthoracic impedance course and an impedance analysis unit, which is connected to the impedance detection unit and analyzes the impedance course, as well as a system and a method for analyzing the impedance course. The analysis of the impedance course is performed in each case with the goal of recognizing a decompensation as early and precisely as possible.

2. Description of the Related Art

In patients who suffer from cardiac insufficiency, acute worsening of their state may occur at irregular intervals, connected with a complete collapse of performance capability, respiratory distress, and fear of suffocation. In this case, immediate hospitalization with emergency treatment must be performed.

These events are caused by a so-called "decompensation", in which the heart is no longer capable of providing a sufficient pumping delivery rate. This event gives notice several weeks beforehand by a (strengthening) rise of the pressure in the pulmonary circulation, and an increasing storage of water in the pulmonary tissue connected thereto, which is not typically perceived in a timely manner by the patient, however.

The occurrence of a decompensation, connected with a great strain of the patient and of the cardiopulmonary system itself, significantly worsens the clinical picture of the cardiac insufficiency. The life expectancy of the patient may be significantly increased by timely recognition of looming decompensations. The costs of medical care may be reduced by the possible avoidance of the hospitalization necessary due to a critical state of the patient.

A device which generates a warning upon initiation of a decompensation in a timely manner before the acute phase is required for this purpose. Appropriate therapy measures may then be introduced early and a hospitalization may be prevented.

Patients who suffer from heart failure are increasingly provided with an implantable defibrillator (ICD), because parts of this patient group also have an increased risk for life-threatening tachyarrhythmias.

The ICDs used are implemented as single-chamber or dual-chamber systems. Approximately ⅔ of all patients having heart failure sufferer from systolic heart failure, in which the efficiency of the blood ejection is greatly worsened (e.g., caused by a left bundle branch block). Such patients are currently increasingly treated using an implant, which reproduces the synchronicity of the contraction of the left and right heart by synchronous stimulation of the right and left heart. They thus receive a so-called cardiac resynchronization therapy (CRT), in which a pacemaker or ICD receives separate electrodes to the right and left ventricles (via the coronary sinus).

A physical parameter, using which the increasing accumulation of liquid in the thorax may be ascertained, is the transthoracic electrical impedance. If the liquid content in the pulmonary tissue increases, the measured impedance drops. With the aid of an implant and the implanted electrodes, this transthoracic impedance may be measured easily. A decompensation may thus be recognized early before the acute phase and thus the patient or physician may be warned to then initiate therapeutic measures.

Devices which measure the transthoracic impedance between the implant housing and/or one or more cardiac electrodes to detect a liquid accumulation in the lungs are known (U.S. Pat. No. 5,957,861, U.S. Pat. No. 6,076,015, U.S. Pat. No. 6,454,719, US 2006/0041280, US 2006/0258952, US 2006/0264776). In general, the impedance values are averaged over a longer period of time (e.g., over 24 hours), to compensate for the impedance variations caused by the cardiac and respiratory cycles and circadian oscillations. These averaged values are used as the basis for the early recognition of looming pulmonary edemas; see Yu C M, Wang L, Chau E, Chan R H, Kong S L, Tang M O, Christensen J, Stadler R W, Lau C P. "Intrathoracic impedance monitoring in patients with heart failure: correlation with fluid status and feasibility of early warning preceding hospitalization." Circulation 2005; 112(6):841-8.

Secondary effects which are not caused by the occurrence of a pulmonary edema may also strongly influence the transthoracic impedance and simulate or conceal a liquid accumulation. These interferences must be compensated for in their influence on the detection of an occurring pulmonary edema.

One of these interferences may arise due to oscillations of the blood conductivity, caused by a changing hematocrit or the varying electrolyte content in the blood, for example.

Systems which determine the blood conductivity and use it for correction of the transthoracic impedance to reduce the influence of the blood conductivity have been described (US 2006/0041280, US 2006/0258952, US 2006/0264776).

The impedances of lung tissue and blood have a differing frequency characteristic. A system has been described which performs the impedance measurement at various frequencies for this reason, to minimize the influence of the blood conductivity (EP 1 665 983).

Changes of the body position (e.g., standing up or lying down) result in a liquid redistribution in the body and thus a temporary change of the liquid content in the lungs. The changes in the liquid content are reproduced in principle by the transthoracic impedance and possibly evaluated as an occurring pulmonary edema. For this reason, systems have been described which detect the body position or its change and incorporate it in the evaluation of the transthoracic impedance (US 2006/0041280, US 2006/0258952, US 2006/0264776). Further interferences may arise due to liquid accumulations in the implant pocket or migration of the implant.

All of these solutions have the disadvantage that additional sensors or additional measurements are necessary. The energy required for this purpose may result in a significant decrease of the service life in long-term implants in particular.

Systems have also been described which monitor the respiratory activity itself to conclude a worsening of the clinical picture from the ascertained respiratory frequency or the respiratory rhythm (e.g., shortness of breath, Cheyne-Stokes breathing, sleep apnea) (U.S. Pat. No. 5,876,353, U.S. Pat. No. 5,957,861, U.S. Pat. No. 6,076,015, U.S. Pat. No. 6,449,509, U.S. Pat. No. 6,454,719, US 2006/0258952).

However, the respiratory activity is first noticeably influenced in a relatively late stage of the pulmonary edema, see Zipes, D. P. et al. [ed.]: Braunwald's Heart Disease; Elsevier, 2005. In addition, however, respiration is also influenced by many other factors, such as physical stress, speaking, and general state of health (NYHA). The decisive early recognition of a pulmonary edema solely from the respiration is thus very susceptible to error. Thus, for example, the dependence of the impedance on the respiration is also exploited to determine the respiratory minute volume, which is used to estimate the metabolic load and employed to activate a frequency-adaptive pacemaker (U.S. Pat. No. 6,076,015, U.S. Pat. No. 6,449,509).

Furthermore, methods have been described which determine hemodynamic variables via an intracardially measured impedance and derive a change of the clinical picture from their change. The dynamics of the heartbeat itself are determined and oscillations which are caused by respiration and by other influences are removed by averaging, for example (Zima, E., et al. "Determination of left ventricular volume changes by intracardiac conductance using a biventricular electrode configuration." Europace 8.7 (2006): 537-44; Stahl, C., et al. "Intracardiac Impedance Monitors Hemodynamic Deterioration in a Chronic Heart Failure Pig Model." J. Cardiovasc. Electrophysiol. 18 (2007): 985-90; EP 1 510 173).

Systems are also known which combine multiple different parameters to judge the clinical picture better and be able to compensate for the uncertainties of an individual parameter (U.S. Pat. No. 5,876,353, U.S. Pat. No. 5,957,861, US 2006/0258952, US 2006/0264776).

The known solutions have various disadvantages.

A decisive disadvantage of the known solutions is based in the fact that the transthoracic electrical impedance is not only influenced by the increasing liquid accumulation in the lungs, but rather also by many other factors. Due to the influences of the secondary factors, the sensitivity and specificity during the lung water detection are reduced. Therefore, the secondary influencing factors must be compensated for by additional parameters or additional measured variables, partially also from other sensors (e.g., body position, intracardial pressure sensors). Additional measurements increase the effort and the power consumption. The service life of the system is decreased by the increased power consumption, above all in long-term implants. The known respiration parameters are also dependent on many other factors and less specific when taken alone. The use of additional parameters is thus also necessary for this purpose.

BRIEF SUMMARY OF THE INVENTION

The invention is based on the object of specifying a device and a method that avoids the disadvantages of the prior art as much as possible, are easy to implement, and in particular offer the highest possible sensitivity and specificity.

This object is achieved according to the invention by an implant having an impedance detection unit for determining a transthoracic impedance course and an impedance analysis unit, which is connected to the impedance detection unit, the impedance analysis unit being implemented to determine the degree of modulation for a particular impedance course detected by the impedance detection unit.

The present invention is fundamentally based on the measurement of the normal transthoracic electrical impedance. However, in contrast to the known methods, no absolute impedance values are used for the detection of the increasing liquid accumulation in the lungs and/or for evaluating the degree of an existing cardiac insufficiency. The direct modulation of the impedance by the respiratory cycle and/or the circadian cycle of the impedance is exploited for detection of the development of a pulmonary edema. The influences of secondary factors on the absolute transthoracic impedance are compensated for or eliminated by the analysis of the modulation parameters. The modulation parameters also react sensitively to liquid accumulations in the lungs, so that an early detection of a developing pulmonary edema is also possible without additional measurements or sensors.

The implant according to the invention measures an electrical impedance in the body in such a way that the lungs are entirely or partially detected by the electrical field generated for the impedance measurement (transthoracic impedance). The implant may be a cardiac pacemaker or an implantable cardioverter/defibrillator (ICD) or also be implemented solely as a monitoring implant having measuring function and preferably contains an apparatus for telemetry communication with an external patient device. The measurement of the transthoracic impedance is preferably performed in a known way between a cardiac electrode and the implant housing, for example. Any electrode configuration, whose electrical field entirely or partially detects the lungs, is usable in principle. Electrodes having multiple contacts may also be used. The measuring current may be supplied via one contact (and/or contact pair) while the dropping voltage is measured via the other contact (and/or contact pair). Although this multipolar measuring configuration has many advantages, it is not a condition for the described invention.

Various suitable and preferred variants result for the impedance analysis unit according to the invention, as may be inferred from the following more detailed description of the invention.

The impedance analysis unit may be a component of the implant itself or also a component of an external device, such as a patient device or a service center, which is to be telemetrically connected, for example, directly or indirectly to the impedance-measuring implant and may thus receive the impedance values detected by the implant.

BRIEF DESCRIPTION OF THE DRAWINGS

The invention will be explained in greater detail on the basis of exemplary embodiments with reference to the figures. In the figures.

DETAILED DESCRIPTION OF THE INVENTION

Figure 1:
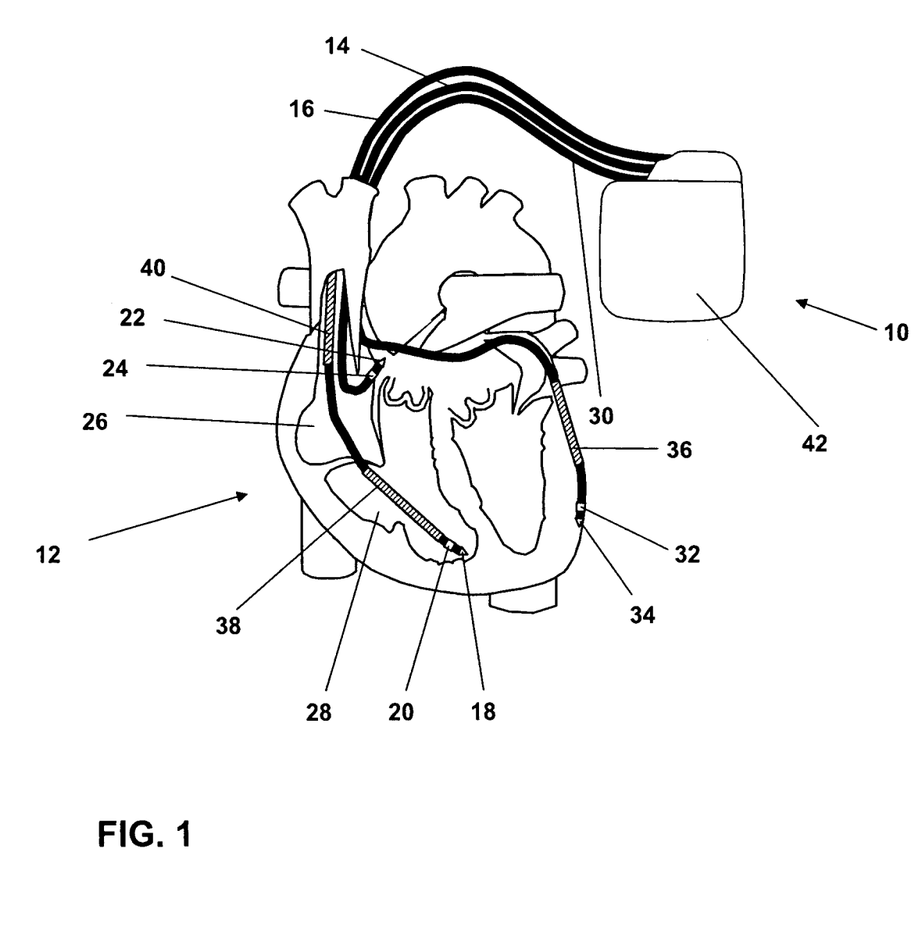
FIG. 1 shows an implant according to the invention in an external illustration

FIG. 1 shows an implant 10 in the form of a biventricular three-chamber cardiac pacemaker and cardioverter/defibrillator (ICD). Three electrode lines are connected thereto, namely a right-atrial electrode line 14, a right-ventricular electrode line 16, and a left-ventricular electrode line 30. In the implanted state, the right-atrial electrode line 14 terminates in the right atrium 26 of a heart 12. The right-ventricular electrode line 16 terminates in the right ventricle 28 of the heart 12 and the left-ventricular electrode line 30 extends via the coronary sinus of the heart 12 up to the left ventricle of the heart.

The right-atrial electrode line 14 carries a right-atrial tip electrode 22 on its distal end and a right-atrial ring electrode 24 at a short distance therefrom. In a similar way, the right-ventricular electrode line 16 carries a right-ventricular tip electrode 18 on its distal end and a right-ventricular ring electrode 20 at a short distance therefrom. A left-ventricular tip electrode 34 is also attached on the distal end of the left-ventricular electrode line 30 and a left-ventricular ring electrode 32 is attached at a short distance therefrom. These electrodes are used to record electrical potentials in the particular heart chamber and to deliver stimulation pulses to the particular heart chamber in normal pacemaker operation. This does not need to be further explained at this point.

The right-ventricular electrode line 16 additionally also carries a right-ventricular shock coil 38, which is situated in the right ventricle in the implanted state, and a second shock coil 40, which is located in the superior vena cava in the implanted state. A left-ventricular shock coil 36 is also attached to the left-ventricular electrode line 30. If needed, the shock coils are used as defibrillation electrodes for delivering defibrillation shocks. This also does not need to be explained in greater detail at this point.

In contrast, it is significant for the present invention that the implant 10 is implemented to deliver a weak subthreshold alternating current, i.e., an alternating current which does not result in tissue contractions, via its metallic conductive housing 42 and the right-ventricular shock coil 38, for example, and to measure the voltage which drops as a result of the supplied alternating current via the right-ventricular tip electrode 18 and a counter pole formed by the electrically conductive hollow housing 42. This allows a transthoracic impedance to be determined in a way known per se.

Figure 2:
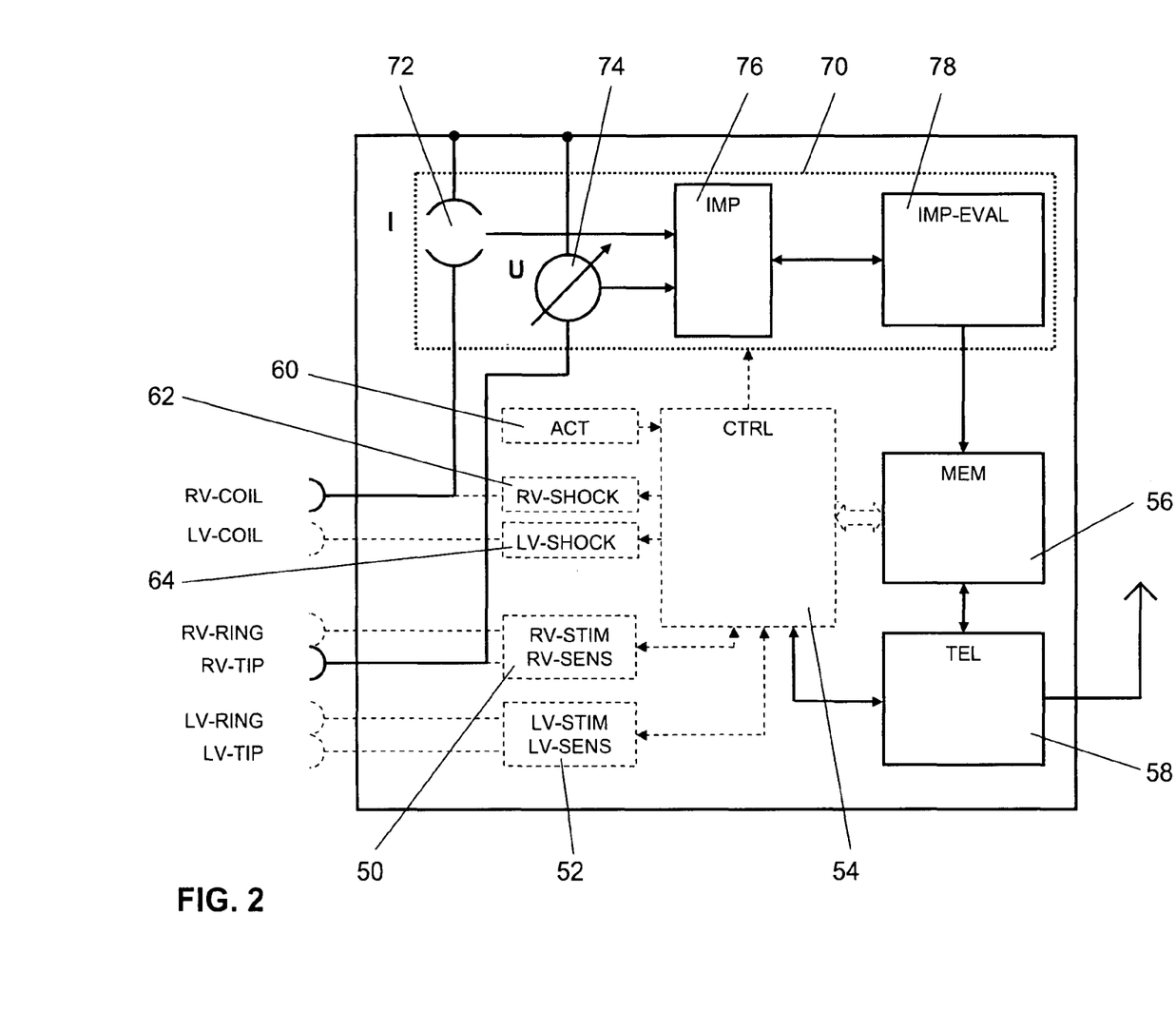
FIG. 2: shows a block diagram of an exemplary design of an impedance analysis unit of the implant according to the invention.

FIG. 2 shows a schematic block diagram of the implant 10 having the typical components of a cardiac pacemaker/cardioverter/defibrillator, namely terminals for the electrode lines shown in FIG. 1 and, connected thereto, electrical components housed in the hollow housing 42, such as a right-ventricular defibrillation shock generator 62, a left-ventricular defibrillation chart generator 64, a right-ventricular sensing and stimulation unit 50 (which are combined into one unit for the sake of simplicity in this illustration), as well as a corresponding left-ventricular stimulation and sensing unit 52. These components are connected to a central control unit 54, which is additionally also connected to an activity sensor 60.

A memory 56 is used to store program data for controlling the control unit 54 and for storing measured values obtained by the implant 10 and operating parameters. The control unit 54 and the memory 56 are additionally connected to a telemetry unit 58, which allows data to be transmitted wirelessly from the implant 10 to an external patient device or, vice versa, data to be received therefrom, such as new control parameters.

Figure 3:
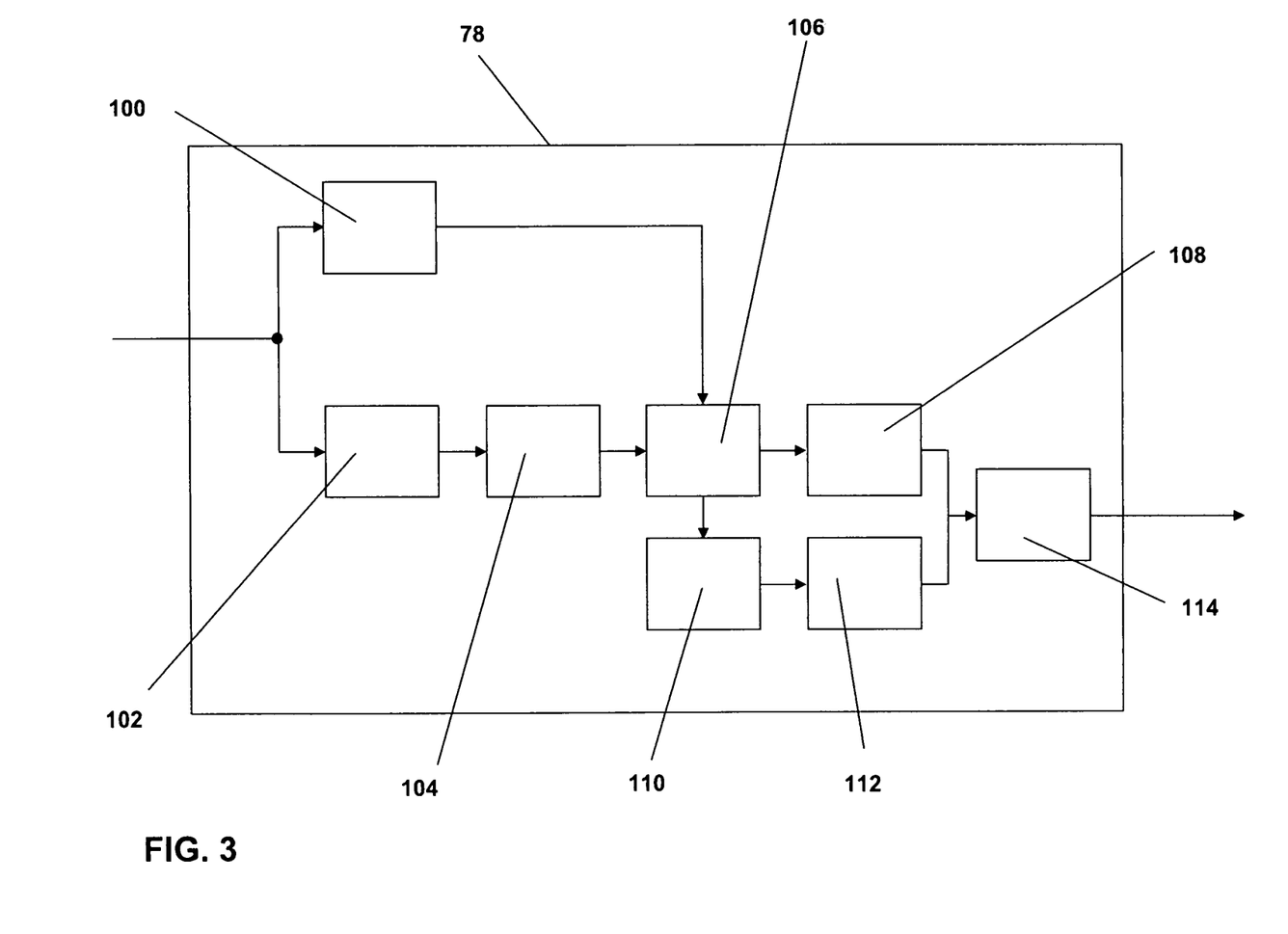
FIG. 3 shows a block diagram of an exemplary design of an impedance analysis unit of the implant according to the invention.

An alternating current source 72, which generates biphasic current pulses in a way known per se and delivers them via the terminal RV coil and the right-ventricular shock coil 38 and via the housing 42 to body tissue lying between them in the implanted state, is significant for the invention. A voltage measuring unit 74 measures the voltage resulting from the delivered alternating current pulses. The strength of the delivered current pulses and the voltage resulting therefrom are analyzed by an impedance detection unit 76 at regular time intervals, so that a chronological sequence of values representing the particular impedance, referred to hereafter as impedance values, results, which reflects the time curve of the impedance between housing 42 of the implant and the right ventricle. This impedance is the transthoracic impedance. An analysis unit 78, which analyzes the impedance as follows, is provided for analyzing this impedance course (see FIG. 3):

The sequence of impedance values originating from the impedance detection unit 76 is first subjected to a digital filtering to determine the mean value M of the impedance course and a respiration signal R by digital filtering using various time constants. A first digital filter 100 is used to determine the mean value M and a second digital filter 102 is used to determine the respiration signal R. An effective value determination unit 104 for determining the effective value of the respiration signal R is connected downstream from the digital filter 102. A ratio determination unit 106, which is connected at a first input to the effective value determination unit 104 and at a second input to the first digital filter 100 and is implemented to calculate the ratio of the effective value of the respiration signal R to the mean impedance M, is in turn connected downstream therefrom. This ratio represents a modulation parameter determined by the impedance analysis unit 78, whose parameter value is compared in a downstream first comparator 108 to a threshold value as a comparison value.

The ratio determination unit 106 is additionally connected at its output to a trend determination unit 110, which calculates the difference between two sequential modulation parameters in each case and compares this difference to a preceding difference. This comparison may also be performed by differentiation. The output signal thus obtained is supplied to a second comparator 112, using which this output signal is compared to a second threshold value as a comparison value.

The output values of the first comparator 108 and the second comparator 112 are supplied to an evaluation unit 114, which generates or does not generate a decompensation warning signal as a function of the two comparison results.

Figure 4:
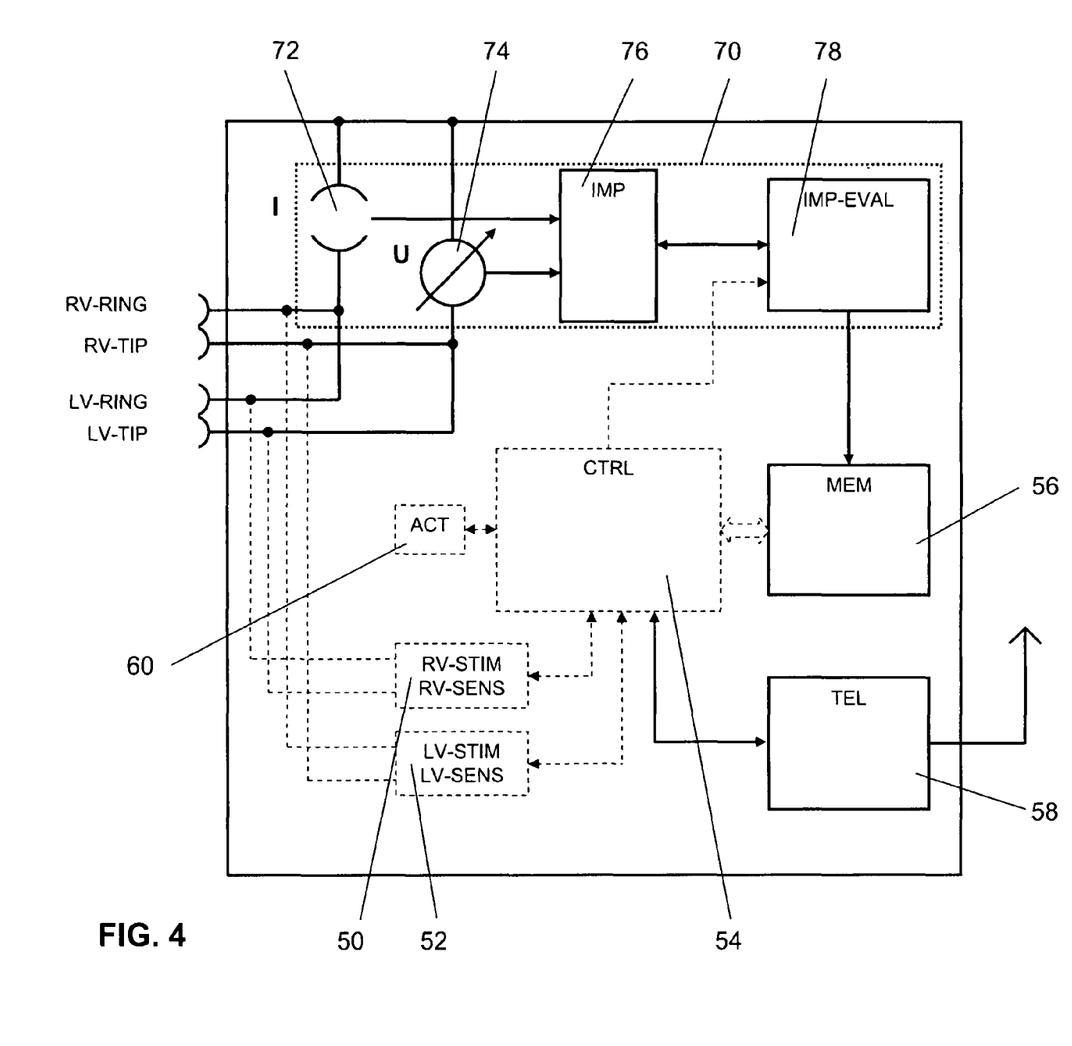
FIG. 4 shows a block diagram of a second exemplary embodiment of the implant according to the invention.

FIG. 4 shows an alternative embodiment variant of the implant 10, in which the alternating current to be delivered to the tissue is delivered on the one hand via the housing 42 of the implant and on the other hand both via the right-ventricular ring electrode 20 and also the left-ventricular ring electrode 32. The voltage measurement is performed on the one hand via the housing 42 of the implant 10 and on the other hand via the right-ventricular tip electrode 18 and the left-ventricular tip electrode 34. Further electrode configurations for measuring the transthoracic impedance are fundamentally known and possible.

The following explanations serve for deeper understanding of the invention and describe further possible embodiments of the impedance analysis unit 78, which are not shown in further figures.

The transthoracic impedance oscillates chronologically around a mean value M, i.e., the impedance is cyclically modulated by the cardiac movements and the respiration. The time curve of the impedance Z(t) is influenced by the relatively high-frequency cardiac movement, which is superimposed on the slower respiratory cycle R.

Figure 5:
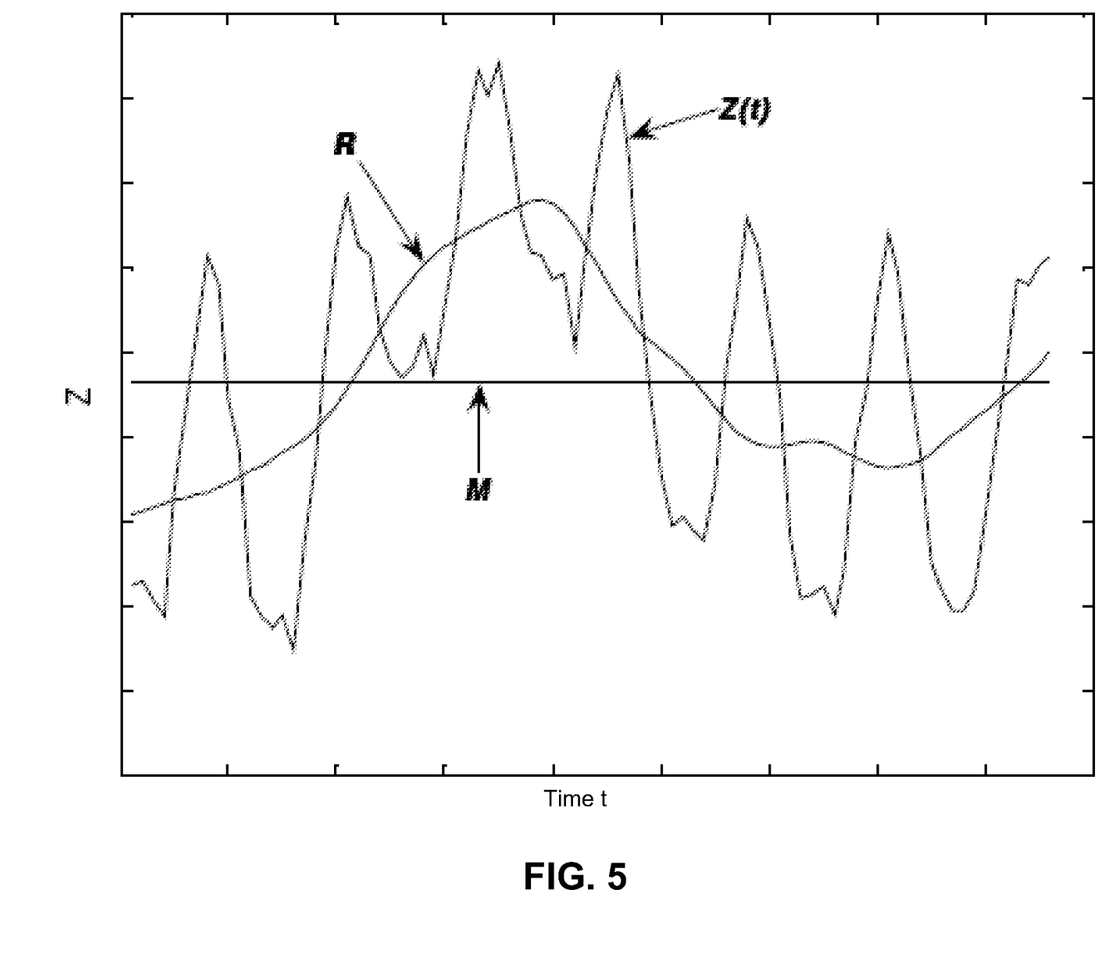
FIG. 5 shows an exemplary illustration of a time impedance course with associated mean value and the respiration signal.

Thus, for example, FIG. 5 shows a time curve of the intrathoracic impedance Z(t) with the associated mean value (M) and the respiration signal (R).

Figure 6:
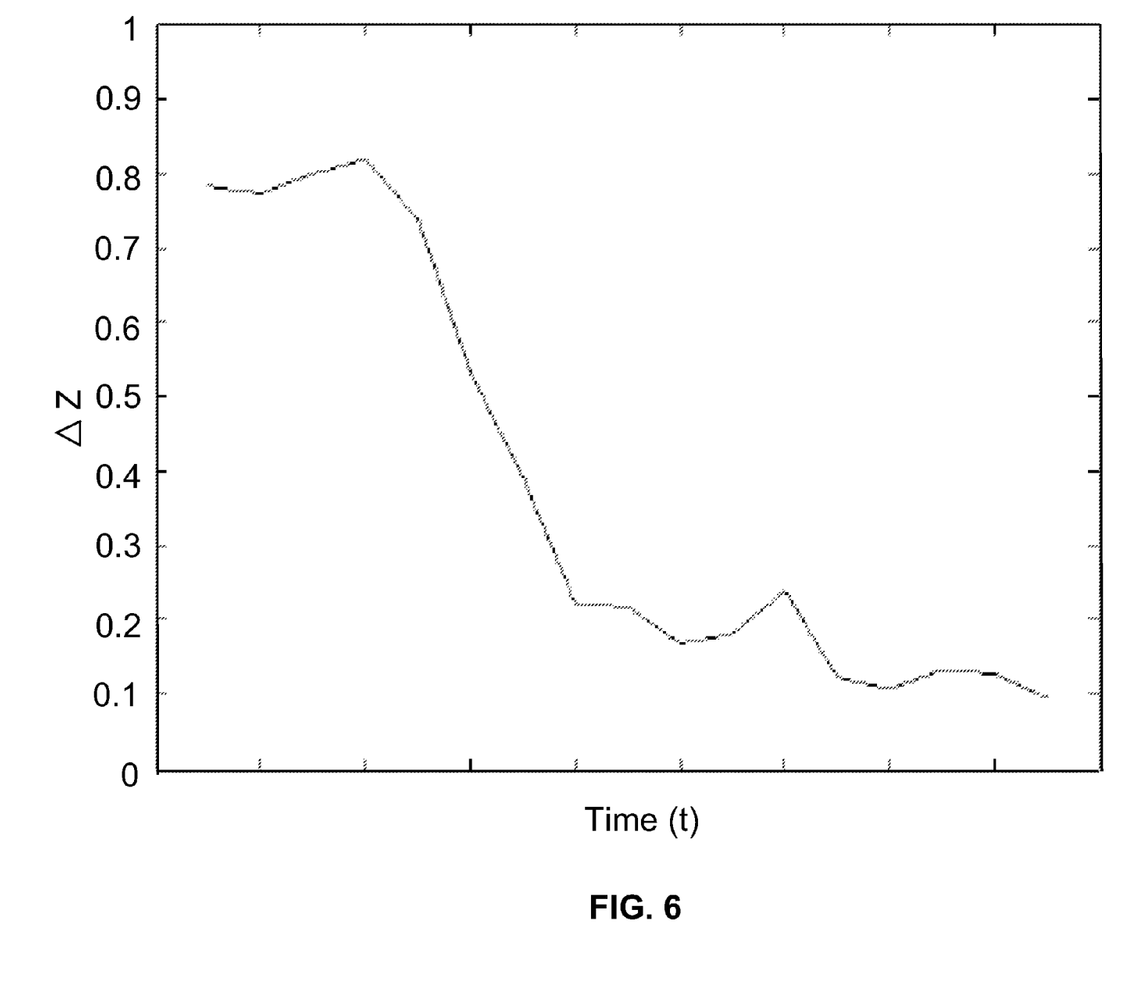
FIG. 6 shows a reduction of the effective value of the respiration signal during the evolution of a pulmonary edema.

The mean impedance value is known to decrease with increasing liquid accumulation in the lungs, which is used by the known methods for pulmonary edema detection. However, it has been established that the modulation of the transthoracic impedance caused by the respiration (respiration signal; R) also significantly decreases in this case, even if respiratory depth and respiratory frequency remain unchanged; see FIG. 6.

The liquid accumulated in the lungs increasingly electrically short-circuits the lung tissue. The influence of the alternating air content in the lungs on the impedance during a respiratory cycle thus decreases. The impedance modulation is coupled directly to the respiration. Other factors, such as changes in the blood conductivity, may thus be separated in their influences, in contrast to the mean impedance. Changes in the respiratory modulation of the transthoracic impedance by the liquid accumulation in the lungs are already detectable well before the respiration is symptomatically impaired.

To be able to determine informative parameters of the respiratory modulation, the component (R) caused by the respiration must be separated from the steady component of the transthoracic impedance (M) and from the component caused by the cardiac cycle (cardiac signal). This is performed by the impedance analysis unit. It may use generally known methods for this purpose, such as various filtering methods or the measurement of the impedance synchronous with the cardiac cycle. These methods resolve the respiration signal R from the time curve of the transthoracic impedance Z(t). Suitable parameters are derived from the resolved respiration signal, which may be used to describe the degree of modulation and to estimate the liquid accumulation in the lungs. The impedance analysis unit is preferably implemented to determine one or more of the following modulation parameters:

effective value or mean amplitude of the respiration signal,
 ratio of effective value or mean amplitude to the mean impedance M,
 relation of the effective value to the respiration frequency,
 interquartile range, this list only having exemplary character and being neither complete nor restrictive. The value of one or more of these modulation parameters is then compared by the impedance analysis unit to a criterion, such as a threshold value, and the detection of a decompensation is decided (e.g., if the threshold value is exceeded). The criterion may have a permanently predefined dimension or be settable individually by patient.

In addition, the impedance analysis unit may also be implemented to record and analyze the trends of one or more modulation parameters over a suitable period of time. The preferred impedance analysis unit may in turn determine suitable trend parameters from these trends, in particular one or more of the trend parameters listed hereafter:

the difference to the preceding parameter value or the change of this difference in relation to the preceding,
 circadian oscillations of the parameter(s),
 changes of the circadian oscillation of the parameter,
 change of the relation between breathing amplitude and respiration frequency.

These trend parameters are also again compared by the impedance analysis unit to a criterion and a decompensation is thus detected. Furthermore, the impedance analysis unit may be implemented to link the parameter trend to the threshold value. Thus, for example, the impedance analysis unit may derive a statement about an occurring decompensation from the duration and the degree which the parameter trend falls below the threshold value.

Figure 7:
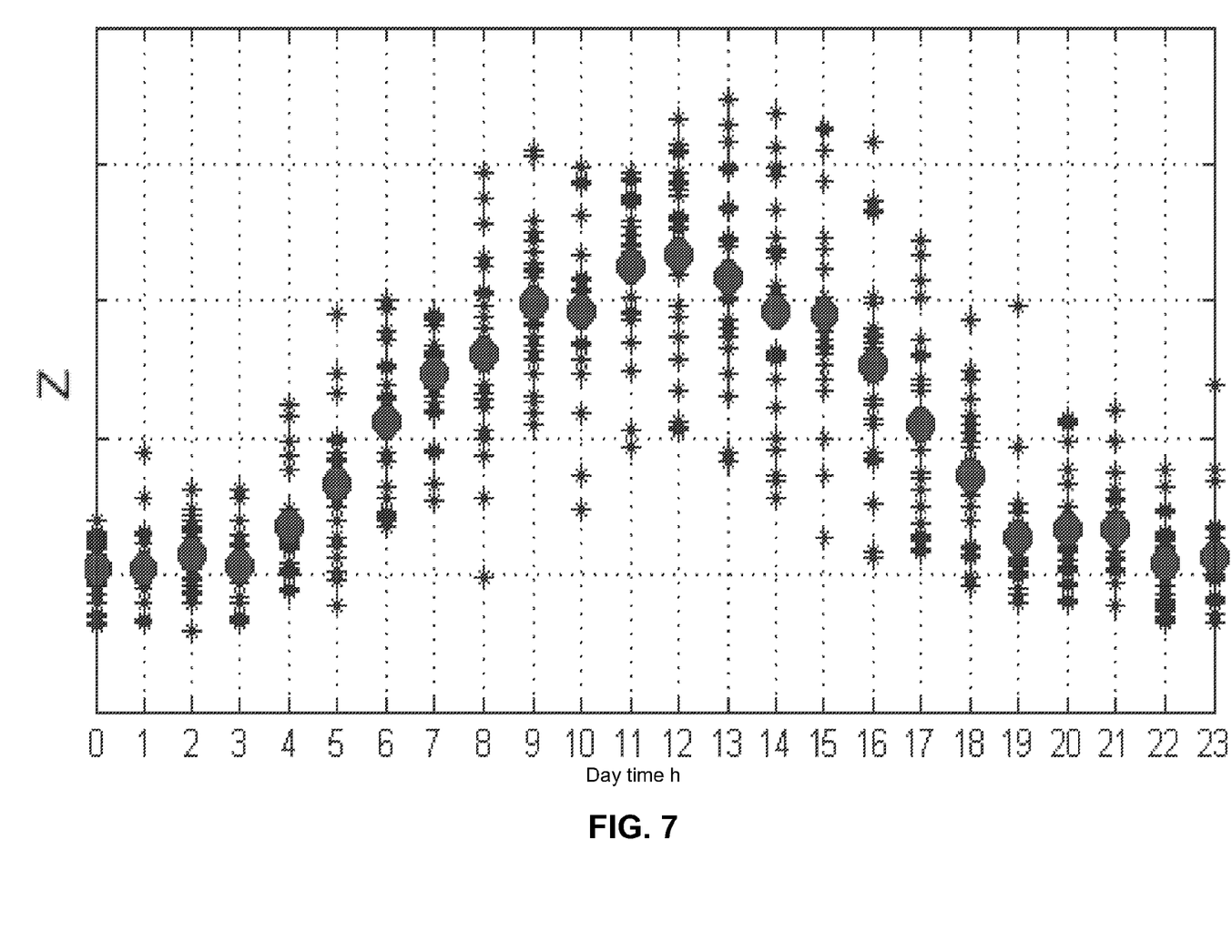
FIG. 7 shows the curve of the trend of the mean impedance.

If one observes the trend of the mean impedance M, one also finds chronological oscillations which indicate a clear circadian rhythm (dependent on the time of day) of the impedance; see FIG. 7.

It is suspected that the circadian pattern of the impedance is to be attributed to liquid displacements in the body, which are linked to other rhythmological (e.g., heart rate) and/or hemodynamic variables (e.g., blood pressure) dependent on the time of day. However, further, e.g., hormonal influencing factors may also play a role. Therefore, the circadian pattern is essentially determined by the clinical picture of the patient in certain circumstances, because recovery phases at night are less pronounced in sick patients than in healthy and/or less sick patients. Therefore, the circadian signal of the impedance and/or parameters derived therefrom are also used for the detection of a pulmonary edema and/or for the evaluation of the existing and/or progressing cardiac insufficiency.

The impedance analysis unit is preferably implemented to ascertain the circadian signal from the mean impedance M by suitable methods, e.g., by hourly averaging of the cyclically measured impedance values. From this circadian signal, in its preferred embodiment the impedance analysis unit in turn determines parameters (circadian parameters), which characterize the signal. The impedance analysis unit is preferably implemented to determine one or more of the circadian parameters cited hereafter:

maximum daily oscillation of the impedance as the difference between maximum and minimum values,
 the ratio of the durations of the two half periods (above and below the daily mean value) to one another,
 phasing of the circadian oscillation, i.e., time of day of the maximum and/or minimum,
 difference of the impedance values of two constant points in time or also the day/night difference.

According to a further preferred embodiment variant, the impedance analysis unit is implemented to also again compare these circadian parameters to a criterion. A statement about an existing or imminent decompensation may be derived therefrom and/or the development of the fundamental cardiac insufficiency may be evaluated. The impedance analysis unit may also further be implemented here to ascertain the trend of one or more circadian parameters over a suitable period of time and derive circadian trend parameters, which may also be compared to a criterion. The impedance analysis unit may also be implemented to link the trend to the criterion to make a statement about the degree of the decompensation.

In addition, the impedance analysis unit may also be implemented to link a circadian parameter or its trend to the trend of a modulation parameter of the respiration signal or the modulation parameter itself, for example:

phase shift between circadian signal and circadian trend of a respiration signal parameter,
 comparison of the respiration signal parameter in only a specific part of the circadian rhythm (e.g., always only at specific times of day or at times of a minimum in the circadian signal).

The impedance analysis unit may also be implemented to evaluate the correlation between one or more parameters of the circadian signal and parameters of the respiration signal and to derive the degree of the decompensation therefrom.

The determination of the parameters and trends and the checking against the corresponding criterion may be performed completely in the implant on the one hand if the impedance analysis unit is integrated completely in the implant. If the impedance analysis unit detects a decompensation by the check against the criterion, the implant may generate an alarm (e.g., acoustically or by vibration or transmit an alarm message via a telemetry connection to an external patient device) or perform independent measures for therapy adaptation, such as the release of medications or the adaptation of their dosing or the adaptation of the stimulation parameters in pacemakers or ICDs.

On the other hand, the implant may only determine the corresponding parameters and transmit them via a telemetry connection to an external patient device. The possible ascertainment of the trends and the check against the criterion may be performed in the patient device. In this case, the impedance analysis unit is at least partially part of the patient device. Upon detection of a decompensation, the patient device may generate an alarm (again, for example, acoustically, or may also notify the physician or a service center via a data connection) or initiate therapeutic measures independently. The patient device may also relay the parameters at suitable time intervals via a data connection to a service center, where the trends may be ascertained and where the check against the criterion may be performed. In this case, at least a part of the impedance analysis unit is a part of the service center. A division of the impedance analysis unit onto the patient device for the pre-analysis and the service center for the trend analysis and the further analysis linked thereto is also possible and advisable. Upon an established decompensation, the service center may send an alarm to the attending physician in a suitable way or provide him with the data for his own judgment in a suitable way. The implant may also only store the impedance values and transmit them at suitable time intervals to the patient device.

The determination of both the parameters and trends and also their check against the criterion may then in turn be performed in the patient device or the service center.

One possible embodiment variant (variant A) comprises an ICD 10 having a defibrillation electrode 38 in the right ventricle. The transthoracic impedance measurement is performed in this case using the current feed via the shock coil 38 and the ICD housing 42 and the voltage measurement via the right-ventricular tip electrode 18 and the ICD housing 42 (see also FIGS. 1 and 2). A sufficiently large part of the lungs is thus included by the measuring path.

To save energy, the impedance is measured once each hour for approximately 30 seconds at a high sampling rate of 32 measurements per second, for example. The implant determines the mean impedance M from these measured values by averaging over all values. Furthermore, the respiration signal is resolved from the measured values via a corresponding digital filter and its effective value is determined. The relative effective value of the respiratory modulation is calculated from the effective value and the mean impedance and stored in the internal trend memory. Once a day at a suitable, fixed time, the daily mean value of the relative effective value is calculated from the trend memory and stored in a long-term memory. If this daily mean value drops more strongly than a fixed measure for longer than a fixed time, this is evaluated as an indicator for a decompensation. For this purpose, for example, the difference between the current and the prior daily mean values are accumulated in a difference sum, if the daily mean value drops. If the daily mean value remains constant or rises, the differential sum is decreased step-by-step again. If the differential sum exceeds a fixed threshold value, this is evaluated as an index for a decompensation and the implant triggers an alarm. It is also possible that the implant transmits the trend memory or the daily mean value to an external patient device via a telemetry connection. The patient device may then perform the calculation and evaluation of the parameters and the triggering of an alarm or relay the data to a service center which takes over the further processing of the data.

A further possible embodiment variant (variant B) again contains an ICD 10 having a defibrillation electrode 38 in the right ventricle. The transthoracic impedance measurement is performed hourly as in variant A. The implant determines the mean impedance from the measured impedance values by averaging over all values and the respiration signal via a corresponding digital signal and calculates its effective value.

Both values are stored in a trend memory 56. The trend memory content is transmitted once a day using the telemetry unit 58 via a telemetry connection to an external patient device 120, which relays the data via an Internet connection to a service center 130; see FIG. 8. In the service center 130, the circadian cycles for the mean impedance and the effective value of the respiration signal are determined. Suitable parameters are determined in each case from these circadian cycles in the service center, such as the maximum daily oscillations and the phasing of both cycles to one another as a time difference between the particular maxima. Daily oscillations and phasing are then compared to predefined threshold values, which may also be predefined as a function of the patient. If one or a suitable combination of threshold values are exceeded, also in combination with other patient data available in the databank, the patient status is classified as "critical" and identified accordingly. In addition, the attending physician may be notified in a suitable way. The physician may then verify the health status of the patient and initiate therapeutic measures if necessary.

Figure 8:
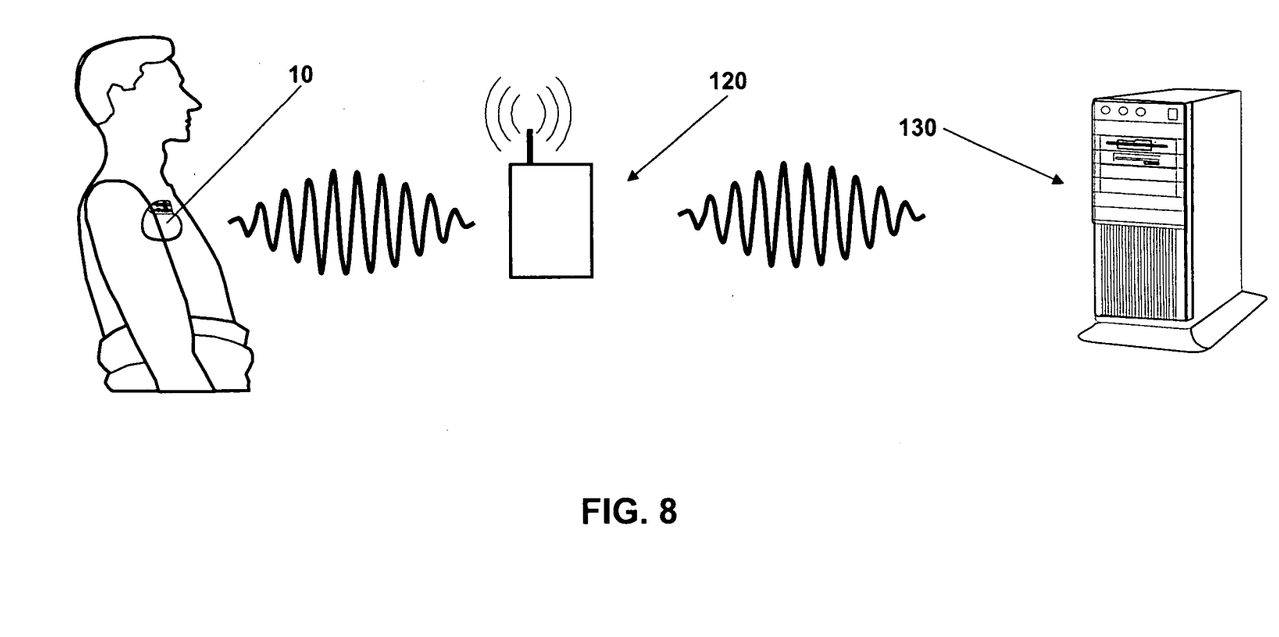
FIG. 8 shows an implant according to the invention in connection with a patient device and a service center.

A further possible embodiment variant (variant C) also contains an ICD 10 having transthoracic impedance measurement as in variant A. The implant 10 again determines the mean impedance hourly, stores it in a trend memory 56, and transmits it to an external patient device 120, which relays the data to a service center 130. The daily mean value of the mean impedance and its circadian cycle are then determined in the service center. The periods of time for falling below (lower half-wave) and exceeding (upper half-wave) the daily mean value are ascertained from the circadian cycle. The ratio of the two periods of time is compared to a predefined threshold value and the patient status is classified as "critical" and identified accordingly if it is exceeded. In addition, the attending physician may be notified in a suitable way. The physician may then verify the health status of the patient and initiate therapeutic measures if necessary.

What is claimed is:

1. A system (10) comprising:
  an impedance detection unit (76) configured to determine impedance values, which represent a transthoracic impedance course;
  an impedance analysis unit (78), which is connected to the impedance detection unit (76);
  wherein the impedance analysis unit (78) is configured to determine a degree of modulation for a particular impedance course detected by the impedance detection unit (76);
  wherein the impedance analysis unit (78) is further configured to
    determine a respiration signal (R) from the transthoracic impedance course and to determine an effective value or mean amplitude of the respiration signal as a modulation parameter that represents the degree of modulation or
    determine the respiration signal (R) from the transthoracic impedance course and to determine a ratio of the effective value or the mean amplitude of the respiration signal to a mean impedance (M) of the transthoracic impedance course as the modulation parameter that represents the degree of modulation or
    determine the respiration signal (R) and a respiration frequency as a frequency of the respiration signal from the transthoracic impedance course and to determine a relation of the effective value of the respiration signal to the respiration frequency as the modulation parameter that represents the degree of modulation wherein the impedance analysis unit (78) is further configured to record trends of one or more modulation parameters over a predefined period of time and to determine trend parameters from these trends or to determine a difference to a preceding modulation parameter value as a trend parameter value wherein the impedance analysis unit (78) is further configured to record trends of one or more modulation parameters comprising a first modulation parameter, a second modulation parameter and a third modulation parameter over a predefined period of time and to determine trend parameters from these trends or to determine a difference to a preceding modulation parameter value as a first trend parameter value, and determine a first difference between said first modulation parameter and said second modulation parameter wherein said first modulation parameter and said second modulation parameter are two sequential modulation parameters and determine a second difference between said second modulation parameter and said third modulation parameter wherein said second modulation parameter and said third modulation parameter are also two sequential modulation parameters and compare said first difference to said second difference as a second trend parameter value; and, wherein the impedance analysis unit (78) is coupled with a first threshold comparator (108) and a second threshold comparator (112) which are respectively configured to compare the first trend parameter value to a first threshold value and compare the second trend parameter value to a second threshold value and to generate a warning signal as a function of whether a respective first and second trend parameter values exceed or fall below the respective first and second threshold value.

2. The system according to claim 1, wherein the impedance analysis unit (78) is implemented to determine circadian oscillations or changes of the circadian oscillations of the one or more modulation parameters as the trend parameter value.

3. The system according to claim 1, wherein the impedance analysis unit (78) is implemented to determine the respiration signal (R) and the respiration frequency as the frequency of the respiration signal from the transthoracic impedance course and to determine a change of a relation between amplitude of the respiration signal and the frequency of the respiration signal as the trend parameter value.

4. The system according to claim 1, wherein the impedance analysis unit (78) is implemented to average cyclically measured impedance values over a predefined period of time and to determine a mean impedance (M) from the cyclically measured impedance values as averaged, and to determine a circadian signal from the mean impedance.

5. The system according to claim 4, wherein the impedance analysis unit (78) is implemented to determine, from the circadian signal, at least one circadian parameter which characterizes the circadian signal.

6. The system according to claim 5, wherein the impedance analysis unit (78) is implemented to determine a particular maximum daily oscillation of the transthoracic impedance course as a difference between maximum and minimum impedance values of a day as the at least one circadian parameter or determine a daily mean value of the transthoracic impedance course and to determine a ratio of a duration of a first half period, during which the transthoracic impedance course runs above the daily mean value, to a duration of a second half period, during which the transthoracic impedance course runs below the daily mean value, as the at least one circadian parameter.

7. The system according to claim 5, wherein the impedance analysis unit (78) is implemented to determine a phase of a circadian oscillation of the transthoracic impedance course in relation to a daily time curve as the at least one circadian parameter or determine a time of day of a maximum and/or minimum of the transthoracic impedance course as the phase of the circadian oscillation of the transthoracic impedance course or determine a difference of impedance values of two constant daily points in time or also a day/night difference as the at least one circadian parameter.

8. The system according to claim 1, wherein the impedance analysis unit (78) is implemented to link a circadian parameter or a trend of the circadian parameter to a trend of a modulation parameter of the respiration signal or the modulation parameter itself, or determine a phase shift between a circadian signal and a circadian trend of a respiration signal parameter, or evaluate a correlation between one or more parameters of the circadian signal and parameters of the respiration signal and to derive a degree of a decompensation therefrom.

9. The system according to claim 1, wherein the system is integrated in an implant (10), which comprises both the impedance detection unit (76) and also the impedance analysis unit (78).

10. The implant (10) according to claim 9, wherein the implant (10) is a cardiac pacemaker or cardioverter/defibrillator.

11. The system according to claim 1, wherein the system comprises an implant (10) having a telemetry unit (58) and an external device (120; 130), which may receive data that represents the impedance values telemetrically from a side of the implant (10), the impedance detection unit (76) being a component of the implant (10) and the impedance analysis unit (78) being a component of the external device (120).

12. The system according to claim 1, wherein the system comprises an implant (10) having a telemetry unit (58) and a service center (130), which is to be connected at least indirectly connected to the telemetry unit (58) of the implant (10) in order to receive data that represents the impedance values from a side of the implant (10), wherein the impedance detection unit (76) is a component of the implant (10) and wherein the impedance analysis unit (78) is a component of the service center (130).

* * * * *